US006659946B1

(12) United States Patent
Batchelor et al.

(10) Patent No.: US 6,659,946 B1
(45) Date of Patent: Dec. 9, 2003

(54) TRAINING SYSTEM (75) Inventors: Stephen Batchelor, Hillsboro, OR (US); Kristin E. Batchelor, Hillsboro, OR (US)

(73) Assignee: Intel Corporation, Santa Clara, CA (US)

(*) Notice: Subject to any disclaimer, the term of this patent is extended or adjusted under 35 U.S.C. 154(b) by 86 days.

(21) Appl. No.: 09/608,993

(22) Filed: Jun. 30, 2000

(51) Int. Cl.[7] .............................. A61B 5/00; A63B 71/00
(52) U.S. Cl. ......................... 600/300; 482/9; 128/920; 705/1
(58) Field of Search .................. 482/1–9; 600/300–301, 600/485, 529, 5; 128/903, 904, 920–925, 897–898; 705/2–4; 434/262, 236–238

(56) References Cited

U.S. PATENT DOCUMENTS

| | | | | |
|---|---|---|---|---|
| 5,544,040 A | * | 8/1996 | Gerbault | 364/401 R |
| 5,822,715 A | * | 10/1998 | Worthington et al. | 702/19 |
| 5,931,764 A | * | 8/1999 | Freeman et al. | 482/4 |
| 5,954,640 A | * | 9/1999 | Szabo | 600/300 |
| 6,050,924 A | * | 4/2000 | Shea | 482/57 |
| 6,233,539 B1 | * | 5/2001 | Brown | 703/11 |

* cited by examiner

Primary Examiner—Max F. Hindenburg
Assistant Examiner—Michael Astorino
(74) Attorney, Agent, or Firm—Schwegman, Lundberg, Woessner & Kluth, P.A.

(57) ABSTRACT

A physical fitness system includes a physical fitness director unit, a training card, an exercise unit, and a shopping unit. The physical fitness director unit generates training information for an individual and stores the information on the training card. The training information includes exercise information and diet information. The training card identifies the individual to the exercise unit and provides information that personalizes the exercise unit to the individual. The training card also identifies the individual to the shopping unit which assists the individual in acquiring groceries that support meal plans prepared by the physical fitness director unit.

9 Claims, 5 Drawing Sheets

TRAINING SYSTEM

FIELD

The present invention relates to a training system, and in particular to a training system capable of being personalized to meet the needs of a particular individual.

BACKGROUND

Diet and exercise are often considered to be two components of a healthy lifestyle. Some experts also believe a person reduces her susceptibility to disease by selecting an appropriate diet and exercising frequently.

A variety of diets and meal plans are available from books, television, and the Internet. Unfortunately, these diets are often not tailored to a particular individual's needs. For example, some diets are tailored to a person who jogs five to ten miles a day. Such a diet is usually not suitable for a person who sits in front of a computer terminal for eight to ten hours a day and does not exercise regularly. In addition, the meal plans that support these diets may include ingredients that are difficult to locate. Furthermore, many of these diets are not easily modified to accommodate a change in an individual's calorie requirements, which may occur from a change in an individual's exercise routine or a change in an individual's level of fitness. A dietitian can provide a meal plan tailored to a particular individual's needs, but for most people the cost of a meal plan prepared by a dietitian is prohibitively expensive.

Exercise routines, such as aerobic exercise routines, strength training routines, and flexibility training routines are also available from books, television, and the Internet. Exercise clubs and gyms provide even more specific exercise opportunities. Following routines provided in books, television or the Internet or in clubs or gyms can often improve an individual's level of fitness. However, these routines are usually directed to broad categories of individuals. For example, an exercise routine, such as a strength training program, may be directed to intermediate weight training students and may meet the needs of a twenty-five year old male, but it will seldom meet the specific needs of a twenty-five year old female who has very aggressive weight training goals. Routine that are not tailored to an individual's needs often do not help the individual efficiently meet her goals. A workout plan from a book also does not provide the motivation that comes from a progress chart that can show the individual where she has come from and where she is headed along the path to her fitness goals. An individual who is unable to efficiently meet her goals due to a lack of a customized exercise program and progress feedback is likely to become discouraged and discontinue her exercise routine.

For these and other reasons there is a need for the present invention.

DESCRIPTION

In the following detailed description of the preferred embodiments, reference is made to the accompanying drawings which form a part hereof, and in which is shown by way of illustration specific preferred embodiments in which the inventions may be practiced. These embodiments are described in sufficient detail to enable those skilled in the art to practice the invention, and it is to be understood that other embodiments may be utilized and that logical, mechanical and electrical changes may be made without departing from the spirit and scope of the present invention. The following detailed description is, therefore, not to be taken in a limiting sense, and the scope of the present invention is defined only by the claims.

Figure 1:
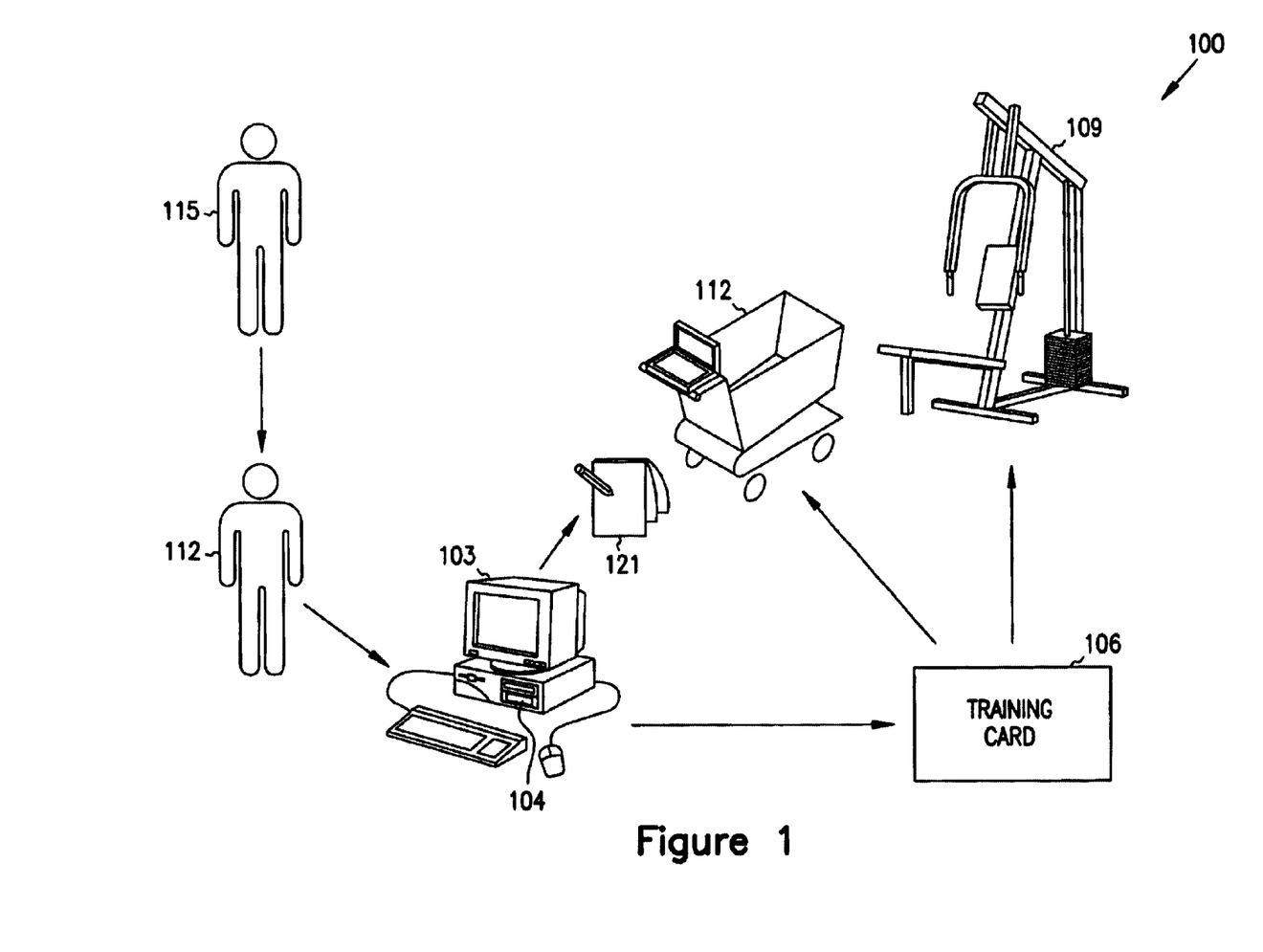
FIG. 1 is a diagram of an example embodiment of a physical fitness system according to the present invention.

FIG. 1 is a diagram of an example embodiment of physical fitness system 100. Physical fitness system 100 includes physical fitness director unit 103, training card 106, exercise unit 109, and shopping unit 112. Physical fitness director unit 103 assists trainer 113 and individual 115 in personalizing training card 106 by storing the training program information for individual 115 on training card 106. The training information stored on training card 106 is provided by a number of different sources. For example, some of the information is provided by trainer 113, some of the information is provided by individual 115, and some of the information is provided by fitness director unit 103. The process of generating training card 106 for a particular individual, such as individual 115, is called personalization, and after personalization, training card 106 is ready for use in connection with exercise unit 109 and shopping unit 112. After collecting the information to personalize training card 106, physical fitness director unit 103 is also capable of generating dietary notes 121 to assist individual 115 in reaching his or her personal physical fitness goals.

Physical fitness director unit 103, in one embodiment, is a computerized system for receiving information related to an individual's health, fitness, and fitness goals. Physical fitness director unit 103 includes computer-readable medium 104. Exemplary types of computer-readable medium 104 include magnetic storage devices, optical storage devices, and solid state semiconductor storage devices. Computer-readable medium 104 is capable of storing computer-executable instructions for personalizing training card 106. During an initial consultation with trainer 113, individual 115 and trainer 113 develop information needed to achieve the health and fitness goals of individual 115. For example, to assist individual 115 in achieving her strength goals, trainer 113 measures the weight, height, shoulder width, distance from the buttocks to knee, and distance from knee to the ground of individual 115. These measurements are provided to fitness director unit 103, stored on training card 106, and used to initialize exercise unit 109 prior to use by individual 115.

Physical fitness director 103 also is also capable of generating a list of exercises, including the number of repetitions and the resistance for each exercise, to assist individual 115 in achieving her personal fitness goals. Physical fitness director 103 also recommends, if requested by individual 115, a diet that complements the exercise program. Dietitians and exercise professionals understand the effects that certain foods (broken up by carbohydrates, proteins, vitamins, minerals, saturated fats, etc.) and combinations of foods, have on human physical development. Physical fitness director 103 uses this knowledge of foods and human development in preparing a recommended diet. Providing individual 115 with exercises and a complementary diet make the overall fitness goals of individual 115 more obtainable.

Information developed during the initial consultation is entered into physical fitness director 103. Physical fitness director 103 processes the information and merges medical and physiological research data with the processed information to generate an exercise program tailored to individual 115. For example, if individual 115 has achieved a high level of cardiovascular fitness at the time of the initial consultation, then the initial exercise program is designed to be more strenuous than if the individual has not achieved a high level of cardiovascular fitness. The exercise program may last from a few weeks to several months, depending on the goals and the initial physical conditioning level of individual 115. After receiving and processing the information developed in the initial consultation, physical fitness director 103 generates a personalized training program including individualized training information and meal plans for individual 115. Physical fitness director 103 also stores the individualized training information and meal plans on training card 106. Information, such as dietary notes 121, may also be printed by physical fitness director 103.

Figure 2:
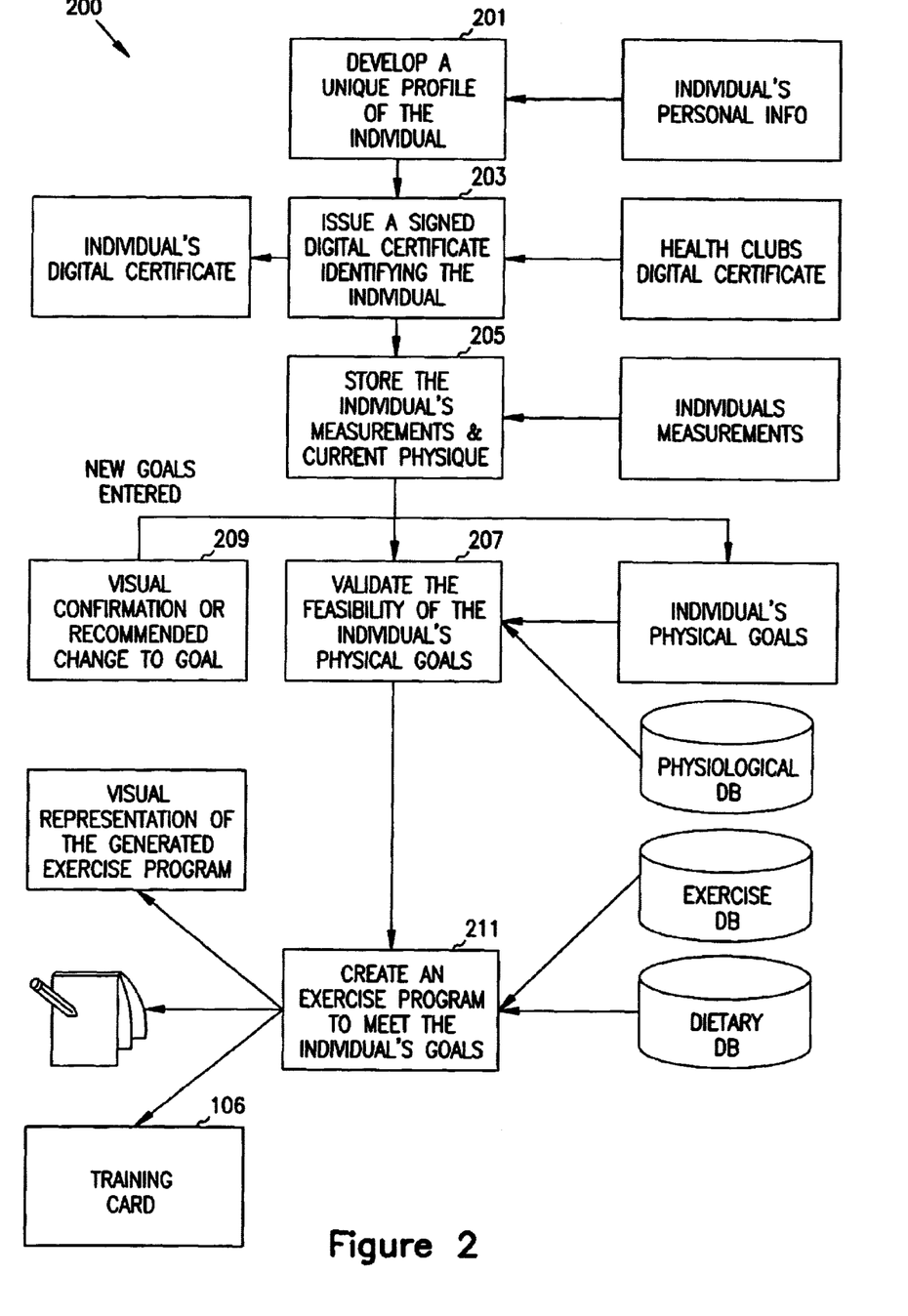
FIG. 2 is a flow diagram of an example embodiment of a method for collecting and processing information to prepare the training card shown in FIG. 1.

FIG. 2 is a flow diagram 200 of an example embodiment of a method according to the present invention for collecting and processing information for use in connection with training card 106. Those skilled in the art can convert the method shown in flow diagram 200 into computer-executable instructions for storage on computer-readable medium 104. As shown in FIG. 2, in preparing training card 106, trainer 113 obtains personal information, such as name, sex, identifying number, billing address, personal fitness goals, and measurements from individual 115. The collected personal information is not limited to the information described above. Other personal information may also be collected and incorporated into the profile. Physical fitness director 103 processes the personal information and generates a unique profile for individual 115 (block 201). After generating a unique profile for individual 115, physical fitness director 103 combines the organization's digital certificate with the unique profile to generate a digital certificate for individual 115 (block 203). Information relating to the measurements and physique of individual 115 are also obtained and stored (block 205). The fitness goals of individual 115 are compared with human anatomical and physiological data stored in a physiological database to validate the feasibility of the physical goals of individual 115 (block 207). If there is a mismatch between the information stored in the database and the individual's goals, suggested changes are displayed by physical fitness director 103. After the suggested changes are displayed, trainer 113 is provided an opportunity to confirm the new goals (block 209). An exercise database and a dietary database are consulted to create an exercise program to meet the goals of individual 115 (block 211). After the exercise program is generated, a visual representation of the exercise program is generated and displayed, and dietary recommendations, including a shopping list and a weekly meal planner, are generated and displayed. Finally, to personalize training card 106, physical fitness director unit 103 stores the digital certificate, one or more measurements, a complete exercise program, and dietary recommendations on training card 106.

After individual 115 and trainer 113 review and agree upon the exercise program generated at block 211, individual 115 receives the training card 106, which includes the personalized training program. Training card 106 includes all the information necessary to identify individual 115 to training unit 109 and to personalize exercise unit 109 to individual 115. Training card 106 also includes a recommended diet and complimentary meal plans. Training card 106 is also capable of controlling and tracking the exercise program. With these capabilities, training card 106 may act as a personal trainer and dietitian for individual 115.

Figure 3:
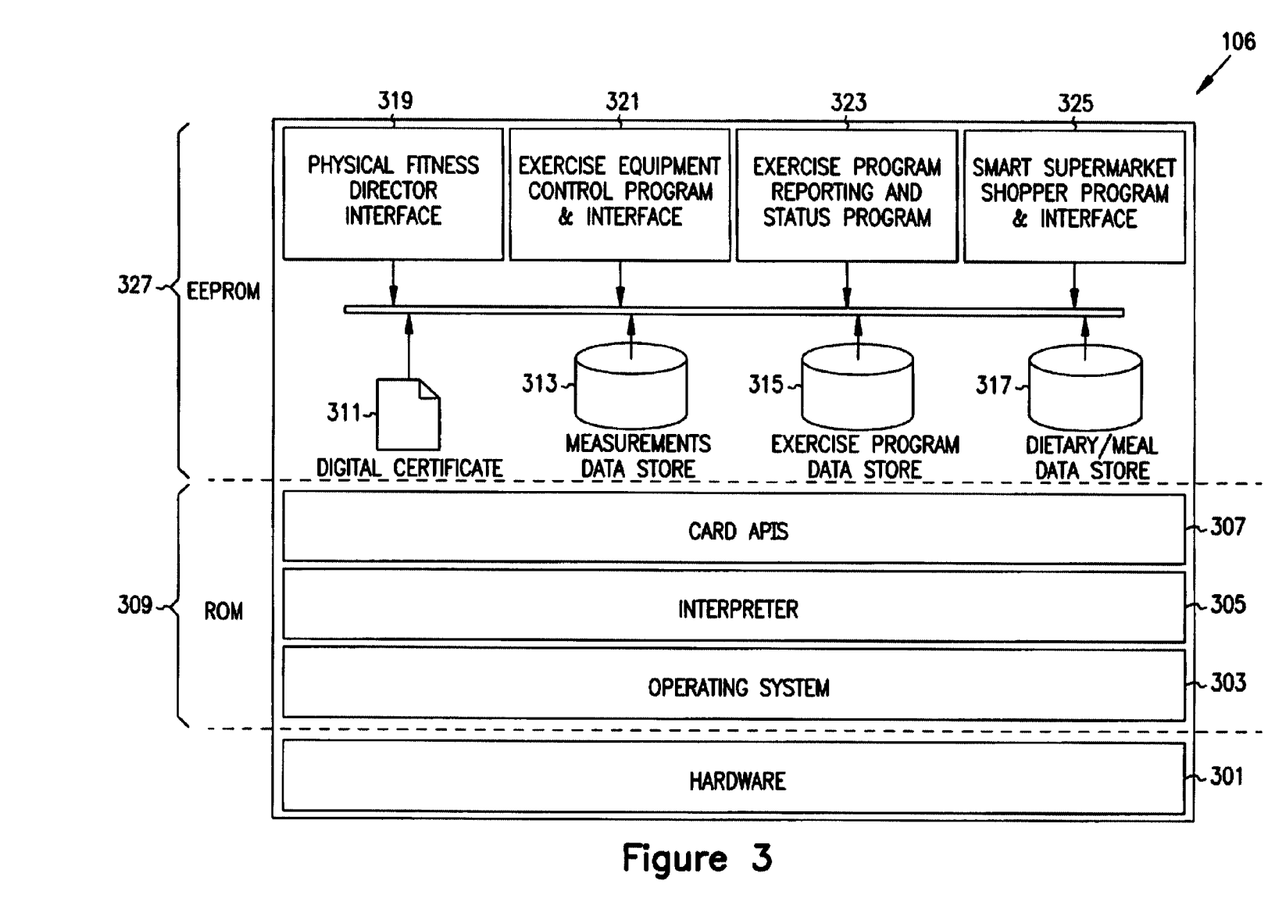
FIG. 3 is an illustration of an example embodiment of a personal training card shown in FIG. 1.

FIG. 3 is an illustration of an example embodiment of training card 106 shown in FIG. 1. In the example embodiment illustrated in FIG. 3, training card 106 is a smart card. Smart cards are known in the information processing industry and are typically programmed for use in connection with a particular data processing application. For example, smart cards are programmed for use in the banking industry as cash cards. In one embodiment of the present invention, a card, similar to a cash card, is programmed and personalized for use in connection with the present invention as training card 106 shown in FIG. 1. After programming training card 106 is capable of exchanging information with shopping unit 112 and exercise unit 109. The information exchanged is information related to the personal training and fitness goals of individual 115 for whom training card 106 is prepared.

Training card 106 is a credit card size device that includes information processing and communications capability. The information processing capability is provided by a processor and the communications capability is provided by a wireless or wired connection. Training card 106 includes hardware 301. In one embodiment, hardware 301 includes a processor, such as a microprocessor. In an alternate embodiment, hardware 301 includes a communication device capable of providing wireless communications. In still another alternate embodiment hardware 301 includes a communications device capable of providing wired communications. Training card 106 also includes software such as operating system 303, interpreter 305, and card application programming interfaces 307. In one embodiment, the software is stored in read-only memory (ROM) 309. Personal information associated with individual 115 is stored in digital certificate 311, measurements data store 313, exercise program data store 315, and dietary/meal data store 317. A number of interfaces, including physical fitness director interface 319, exercise equipment control program and interface 321, exercise program reporting and status program interface 323, and smart supermarket shopper program and interface 325 are also included in EEPROM 327. The number of interfaces provide a flexible solution to the problem of providing an inexpensive personal trainer and dietary consultant to individual 115.

Digital certificate 311 issued by physical fitness director 103 and stored on training card 106 is issued for the purposes of providing individual 115 with controlled access to a fitness club and authentication and identification of individual 115 to each exercise unit 109 and to shopping unit 112.

Measurements data store 313 contains an individual's physical measurements taken during the initial consultation with a health club trainer. Some example measurements described above include current weight, height, shoulder width, distance from the buttocks to knee, and distance from knee to the ground. The majority of these measurements will not change over time, however to keep data store 313 updated, the measurements can be repeated periodically, and measurements data store 313 can be updated with any changed measurements.

Exercise program data store 315 includes an exercise schedule generated by physical fitness director unit 103. The exercise schedule includes a list of the types of exercises to be performed on each piece of available equipment. The list also includes a suggested order for performing the exercises, the number of sets for each exercise, the number of repetitions for each set, and changes in the types of exercises to be performed as the exercise program progresses.

Dietary and meal suggestion data store 317 is also generated by physical fitness director unit 103. Dietary and meal suggestion data store 317 contains daily dietary guidance, with meal suggestions and recipes, which can be used in connection with shopping unit 112. This integration of dietary and meal suggestion data store 317 with shopping unit 112 assists an individual in achieving her overall fitness goals.

Exercise equipment control and interface program 321 allows training card 106 to interact with the different pieces of exercise equipment. Training card 106 provides centralized control for conducting and monitoring an exercise program. An important function of training card 106 is the guidance of the individual from one machine to another. Since training card 106 does not have its own user interface, training card 106 provides information for display on the visual display associated with each piece of exercise equipment. After an exercise is completed, the displayed information includes directions that instruct the individual on which exercise unit to use next. Training card 106 is capable of adjusting the dimensions of each exercise unit to the physical measurements of the individual using the equipment. This tailoring of each piece of exercise equipment to a particular individual reduces the risk of injury to the individual in performing an exercise. In addition, tailoring an exercise unit to an individual provides the individual with a great opportunity to perform the exercise correctly. Training card 106 also controls the number of sets, the number of repetitions per set, the overall resistance for each set, and the resistance deviation for each repetition in a set has over the previous repetition.

A program status and reporting program tracks the progress of the individual through her exercise program. At any time during the exercise program, training card 106 can be entered into a piece of exercise equipment to obtain the current status of the individual's performance. This feedback and visibility to progress helps motivate the individual and will keep her on track with her fitness goals. The progress report also allows the exercise program to be adjusted, if necessary, during the regular consultation sessions between individual 115 and trainer 113.

Smart supermarket shopper program and interface 325 is a dietary feature of physical fitness system 100. Training card 106 uses dietary and meal suggestion data store 317 to generate a list of groceries needed to.prepare the exercise program meal recommendations, which are generated and printed at the initial consultation. Smart supermarket shopper program and interface 325 is capable of interfacing with shopping unit 112, and assists individual 115 in purchasing the meal ingredients necessary to follow the exercise program meal recommendations.

Figure 4:
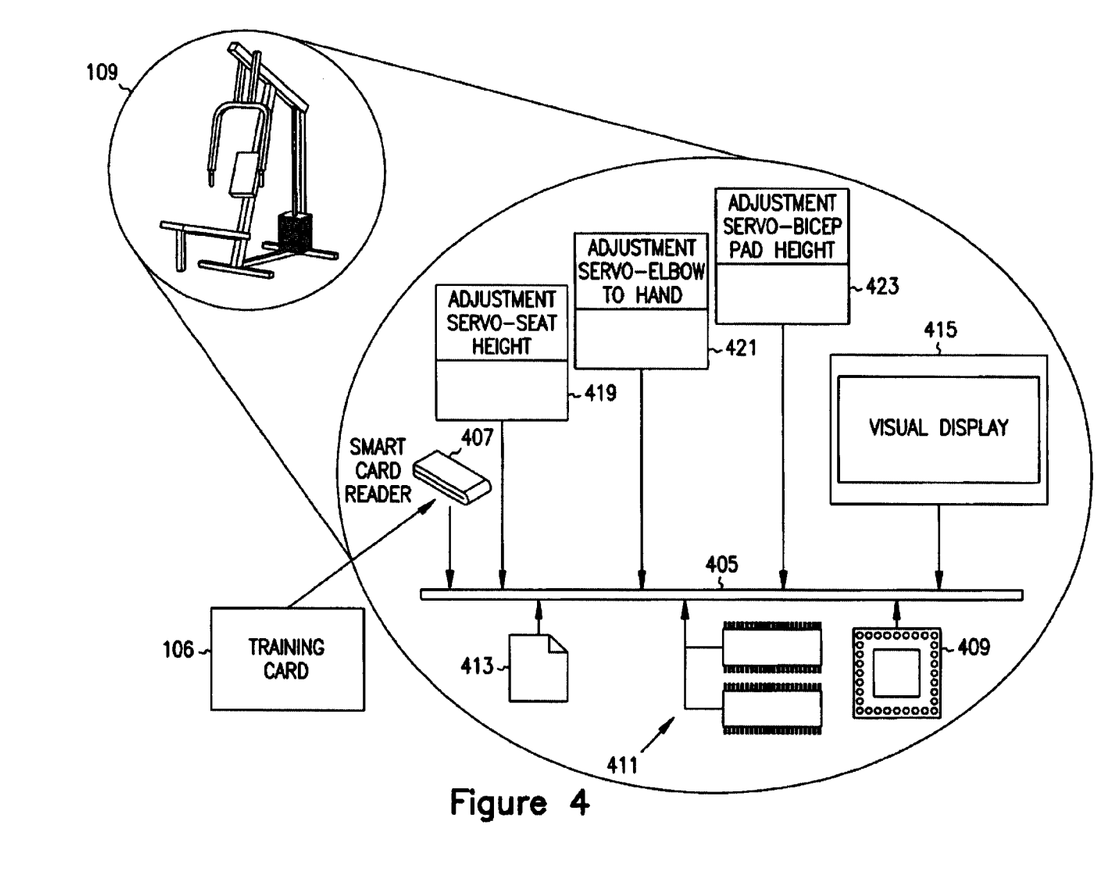
FIG. 4 is a system diagram of an example embodiment of an exercise unit shown in FIG. 1.

FIG. 4 is a system diagram of an example embodiment of exercise unit 109 shown in FIG. 1. Exercise unit 109 provides a platform for exercising specific areas of an individual's body, such as the abdomen, back, legs and arms. Exercise unit 109 includes one or more processing, control, display and data units coupled to system bus 405. Processing units include smart card reader unit 407 and processor unit 409 which communicates with memory unit 411. The control units include seat height control unit 419, elbow-to-hand control unit 421, and biceps pad height control unit 423. The display units include visual display unit 415, and the data units include digital certificate 413.

Processor unit 409 is coupled to system bus 405 and controls the operation of exercise unit 109. Processor unit 409, in one embodiment, is a microprocessor. In an alternate embodiment, processor unit 409 is a reduced instruction set computing (RISC) processor. However, the present invention is not limited to use in connection with a microprocessor or a RISC processor. Any information processing system capable of communicating with a bus coupled to a number of devices is suitable for use in connection with the present invention. Alternatively, any information processing system capable of communicating with the number of devices without a bus is also suitable for use in connection with the present invention. Memory unit 411 is coupled to system bus 405. In one embodiment, memory unit 411 is a solid state memory, such as a dynamic random access memory (DRAM), a static random access memory (SRAM), an electrically programmable read-only memory (EPROM), or an electrically erasable programmable read-only memory (EEPROM). In an alternate embodiment, memory unit 411 is an information storage device, such as a magnetic storage system, optical storage system, or a magneto-optical storage system.

Smart card reader unit 407 is coupled to system bus 405 and communicates with other devices coupled to system bus 405, such as processor unit 409 and memory unit 411. For example, smart card reader unit 407 communicates with training card 106 by reading and writing to training card 106. Card reader units suitable for use in connection with training card 106 are known in the art. Any smart card reader unit capable of reading and writing to training card 106 is suitable for use in connection with the present invention.

The control units include seat height control unit 419, elbow-to-hand control unit 421, and biceps pad height control unit 423. Each of the control units, in one embodiment, is a servo control unit capable of setting the structure being controlled to a particular position and maintaining the structure at the set position. For example, seat height control unit 419 sets and controls the seat height of an exercise seat in exercise unit 109. Servo control units are known in the art, and any unit capable of maintaining position control under the weight of an individual using exercise unit 109 is suitable for use in connection with the present invention.

Visual display unit 415 is coupled to system bus 405 and communicates with other devices, such as smart card reader unit 407 and processor unit 405, which are also coupled to system bus 405. Visual display unit 415 is capable of displaying information for use by an individual using exercise unit 109. Display information includes, but is not limited to, text information, graphical information, pictorial information, video information or some combination of text, graphical, pictorial and video information. For example, in one embodiment, visual display unit 415 provides text information describing a particular exercise, pictorial information showing the proper starting position for performing the particular exercise, and video information showing the proper form for performing the exercise.

Exercise unit 109 is capable of being personalized. For example, in one embodiment, exercise unit 109 is personalized to accommodate a particular individual's physical measurements by adjusting seat height control unit 491, elbow-to-hand control unit 421, and biceps pad height control unit 423. In an alternate embodiment, exercise unit 109 is personalized to support a particular individual's personal exercise plan. To personalize exercise unit 109 to support a personal exercise plan, the dynamic resistance of exercise unit 109 is set to match the resistance required in an individual's personal exercise plan.

Processor 109 receives and processes information to control exercise unit 109. For example, smart card reader 405 reads training card 106 and makes the personal exercise information contained on training card 106 available on system bus 405. Processor unit 409 then reads and processes the information on system bus 405.

To use training unit 109, an individual inserts training card 106 into smart card reader 405 associated with exercise unit 109. Processor unit 409 verifies that digital certificate 413 included in the personal training information is valid. Digital certificate 413 is valid if the certificate has not expired, the certificate has a signature that confirms the authenticity of the certificate, and the certificate is issued from a valid issuer. Certificate authentication is followed by a welcome message displayed on visual display unit 415.

Once training card 106 is authenticated, the adjustable parts of exercise unit 109 are configured to an individual's physical measurements stored on training card 106. The adjustment of exercise unit 109 varies with the type of exercise being performed. For example, for an arm curl the seat pad height is adjusted by seat pad height control unit 419, the biceps rest pad height is adjusted by biceps pad height control unit 423, and the distance between the elbow position and the hand position is adjusted by the elbow-to-hand distance control unit 421. Each of the control units 419, 421, and 423 maintain the position of the corresponding servoed component of exercise unit 109.

After the adjustable parts of exercise unit 109 are configured, training card 106 downloads to exercise unit 109 the exercise for the session. This includes the number of sets the individual is to perform, and the number of repetitions in each set, which may be change as the exercise progresses. The compete set of exercises is listed and the goal highlighted to encourage the individual.

During an exercise, training unit 106 controls the resistance of exercise unit 109. The control extends to controlling the resistance of each repetition in each set. This high degree of control is useful for meeting different training goals. For example, to increase the mass of a muscle, a heavy increasing resistance for a small number of repetitions is most effective. However, to increase the stamina of a muscle, a more moderate resistance which progresses from the moderate resistance to a lighter resistance during a high number of repetitions is most effective. Training unit 106 is also capable of continuously adjusting the resistance throughout a single repetition so that correct and safe exercising occurs. Since many exercise-related injuries occur as a result of exercise performed with a constant resistance applied through the full range of motion in an exercise, this capability reduces the likelihood of injury to a muscle, joint, or tendons during the exercise.

Once an individual completes an exercise on a piece of exercise equipment, the results of the exercise are logged on training card 106. After a count-down timer counts down the rest period time between exercises for the individual and a congratulatory message is communicated to the individual, the individual is instructed to move to the next piece of equipment.

A physical fitness system has been described which includes a physical fitness director unit, a training card, an exercise unit, and a shopping unit. The physical fitness director unit generates training information for an individual and stores the information on the training card. The training information includes exercise information and diet information. The training card identifies the individual to the exercise unit and provides information that personalizes the exercise unit to the individual. The training card also identifies the individual to the shopping unit which assists the individual in acquiring groceries that support meal plans prepared by the physical fitness director unit.

Figure 5:
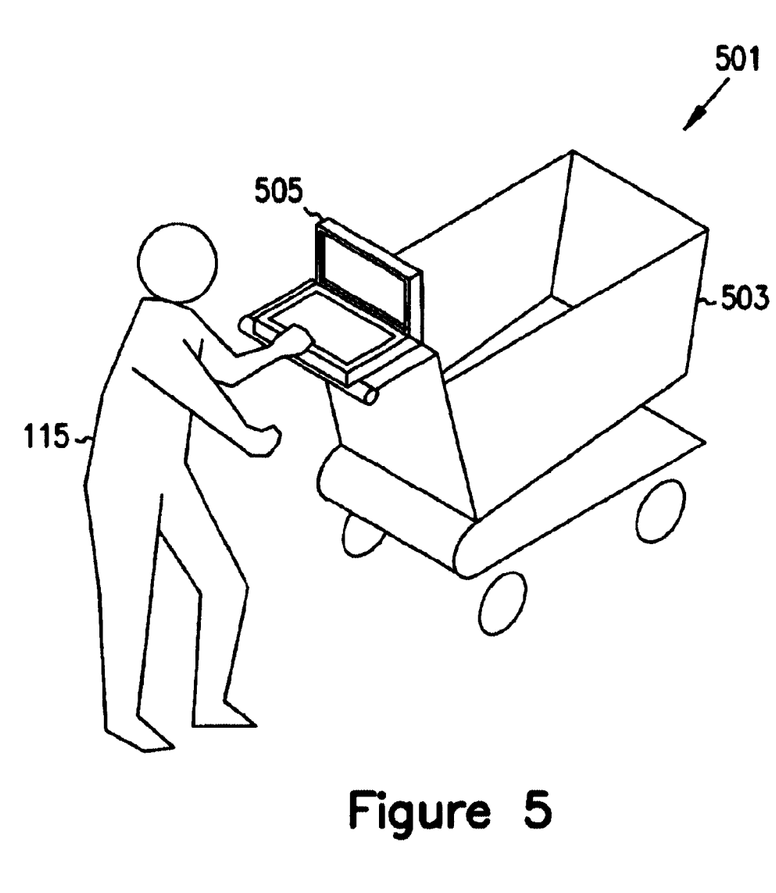
FIG. 5 is an illustration of an example embodiment of a shopping unit suitable for use in connection with the present invention.

FIG. 5 is an illustration of an example embodiment of shopping unit 501 which is suitable for use in connection with the present invention. Shopping unit 501 includes product carrying device 503 and computing device 505. In one embodiment, product carrying device 503 is a push powered shopping cart. In an alternate embodiment, product carrying device 503 is a motor driven shopping cart. In one embodiment, computing device 503 is a personal computer mounted on product carrying device 503 and capable of communicating with training card 106. In operation, computing device 505 communicates with training card 106 to identify meal plans and shopping lists for individual 115. Computing device 505 then provides directions to individual 115 for locating items included in the shopping list. In one embodiment, computing device 505 provides information directing a shopper to an aisle in a supermarket containing an item associated with the meal description. In an alternate embodiment, computing device 505 provides information that directs the shopper to a shelf containing an item associated with a meal description.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is intended that this invention be limited only by the claims and the equivalents thereof.

What is claimed is:

1. A training card comprising:
   a smart card including a memory configured to store a digital certificate, one or more data groups, and one or more personal training unit interfaces, wherein the digital certificate and the one or more data groups are associated with an individual and each of the one or more personal training unit interfaces is associated with an exercise unit, a shopper unit or a physical fitness director unit.

2. The training card of claim 1, wherein the memory comprises an electrically erasable programmable read only memory (EEPROM).

3. The training card of claim 1, wherein at least one of the one or more data groups is a measurements data group containing physiological measurements of the individual.

4. A computer-readable medium having computer-executable instructions stored thereon for performing a method of personalizing a training card, the method comprising:
   creating a health profile for an individual;
   processing the health profile to generate an exercise plan for the individual;
   forming a wireless communication connection between a computerized system and the training card; and
   storing the health profile and the exercise plan on the training card.

5. The computer-readable medium of claim 4, further comprising:

generating a digital certificate containing information concerning the individual and storing the digital certificate on the training card.

6. A computer-readable medium having computer-executable instructions stored thereon for performing a method of personalizing a training card, the method comprising:
   creating a health profile for an individual;
   processing the health profile to generate an exercise plan for the individual;
   storing the health profile and the exercise plan on the training card;
   processing the health profile to generate a diet for the individual; and
   storing the diet on the training card.

7. A computer-readable medium having computer-executable instructions stored thereon for performing a method of personalizing a training card, the method comprising:
   creating a health profile for an individual;
   processing the health profile to generate an exercise plan for the individual;
   storing the health profile and the exercise plan on the training card;
   processing the health profile to generate a diet for the individual; and
   storing the diet on the training card, wherein creating the health profile for the individual comprises:
      identifying a current weight for the individual;
      identifying a target weight for the individual; and
      storing the target weight on the training card.

8. A computer-readable medium having computer-executable instructions stored thereon for performing a method of personalizing a training card, the method comprising:
   creating a health profile for an individual;
   processing the health profile to generate an exercise plan for the individual;
   storing the health profile and the exercise plan on the training card;
   processing the health profile to generate a diet for the individual; and
   storing the diet on the training card, wherein processing the health profile to generate an exercise plan for the individual comprises:
      preparing a sequence of weight resistance exercises appropriate to the individual.

9. A computer-readable medium having computer-executable instructions stored thereon for performing a method of personalizing a training card, the method comprising:
   creating a health profile for an individual;
   processing the health profile to generate an exercise plan for the individual;
   storing the health profile and the exercise plan on the training card;
   processing the health profile to generate a diet for the individual; and
   storing the diet on the training card, wherein processing the health profile of the individual to generate a diet for the individual comprises:
      identifying one or more meal plans; and
      storing the one or more meal plans on the training card.

* * * * *